US008343113B2

(12) United States Patent
Hokanson

(10) Patent No.: US 8,343,113 B2
(45) Date of Patent: Jan. 1, 2013

(54) MEDICAL VALVE ASSEMBLY

(76) Inventor: Charles Hokanson, Edgewater, FL (US)

( * ) Notice: Subject to any disclaimer, the term of this patent is extended or adjusted under 35 U.S.C. 154(b) by 0 days.

(21) Appl. No.: 13/271,546

(22) Filed: Oct. 12, 2011

(65) Prior Publication Data
US 2012/0089086 A1 Apr. 12, 2012

Related U.S. Application Data

(60) Provisional application No. 61/392,063, filed on Oct. 12, 2010, provisional application No. 61/474,925, filed on Apr. 13, 2011.

(51) Int. Cl.
A61M 5/00 (2006.01)
(52) U.S. Cl. ...................................... 604/256
(58) Field of Classification Search .................. 604/246, 604/247, 256
See application file for complete search history.

(56) References Cited

U.S. PATENT DOCUMENTS

| 4,080,965 A | 3/1978 | Phillips |
| 4,121,585 A | 10/1978 | Becker, Jr. |
| 4,511,359 A | 4/1985 | Vaillancourt |
| 4,512,766 A | 4/1985 | Vailancourt |
| 4,617,012 A | 10/1986 | Vaillancourt |
| 4,950,260 A | 8/1990 | Bonaldo |
| 5,065,783 A | 11/1991 | Ogle, II |
| 5,122,123 A | 6/1992 | Vaillancourt |
| 5,273,533 A | 12/1993 | Bonaldo |
| 5,423,791 A | 6/1995 | Bartlett |
| 5,470,319 A | 11/1995 | Mayer |
| 5,474,536 A | 12/1995 | Bonaldo |
| 5,474,544 A | 12/1995 | Lynn |
| 5,549,651 A | 8/1996 | Lynn |
| 5,616,129 A | 4/1997 | Mayer |
| 5,676,346 A | 10/1997 | Leinsing |
| 5,685,866 A | 11/1997 | Lopez |
| 5,699,821 A | 12/1997 | Paradis |
| 5,807,348 A | 9/1998 | Zinger et al. |
| 5,814,024 A | 9/1998 | Thompson et al. |
| 5,879,336 A | 3/1999 | Brinon |
| 5,957,898 A | 9/1999 | Jepson et al. |
| 6,089,541 A | 7/2000 | Weinheimer et al. |
| 6,142,446 A | 11/2000 | Leinsing |
| 6,171,287 B1 | 1/2001 | Lynn et al. |
| 6,183,448 B1 | 2/2001 | Mayer |
| 6,482,188 B1 | 11/2002 | Rogers et al. |
| 6,651,956 B2 | 11/2003 | Miller |
| 6,706,022 B1 | 3/2004 | Leinsing et al. |

(Continued)

OTHER PUBLICATIONS

International Search Report for corresponding PCT Application No. PCT/US2011/055912, dated May 22, 2012.

Primary Examiner — Aarti B Berdichevsky
(74) Attorney, Agent, or Firm — Caesar, Rivise, Bernstein, Cohen & Pokotilow, Ltd.

(57) ABSTRACT

A medical valve assembly including a rigid external housing and a valve stem of a resilient material. The valve stem includes a passageway for conveying a fluid which has an hourglass shape to create a venturi effect when cleaning the valve stem to improve the efficiency of the cleaning process. The passageway also includes no sharp edges, thus reducing the risk of fluid getting trapped inside the passageway when the medical valve assembly is not in use. Even further, when a needleless syringe is removed from the valve stem, the valve stem expands to an uncompressed state with its top end being generally flush with an end of the housing to present a swabable surface for cleaning purposes.

21 Claims, 7 Drawing Sheets

U.S. PATENT DOCUMENTS

| | | |
|---|---|---|
| 6,808,161 B1 | 10/2004 | Hishikawa |
| 6,875,205 B2 | 4/2005 | Leinsing |
| 6,979,323 B2 | 12/2005 | Rogers et al. |
| 7,025,744 B2 | 4/2006 | Utterberg et al. |
| 7,104,520 B2 | 9/2006 | Leinsing et al. |
| 7,118,560 B2 | 10/2006 | Bonaldo |
| 7,241,285 B1 | 7/2007 | Dikeman |
| 7,252,652 B2 | 8/2007 | Moorehead et al. |
| 7,329,249 B2 | 2/2008 | Bonaldo |
| 7,520,489 B2 | 4/2009 | Ruschke et al. |
| 7,559,530 B2 | 7/2009 | Korogi et al. |
| 7,753,338 B2 | 7/2010 | Desecki |
| 7,947,032 B2 | 5/2011 | Harding et al. |

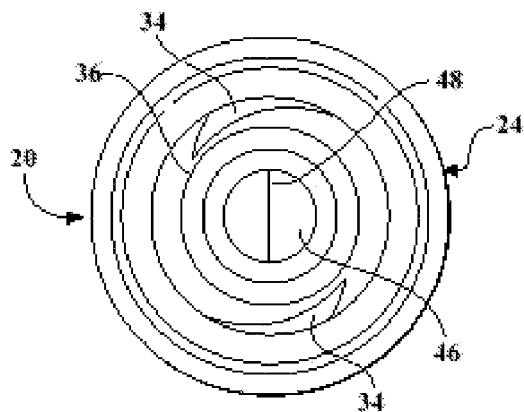
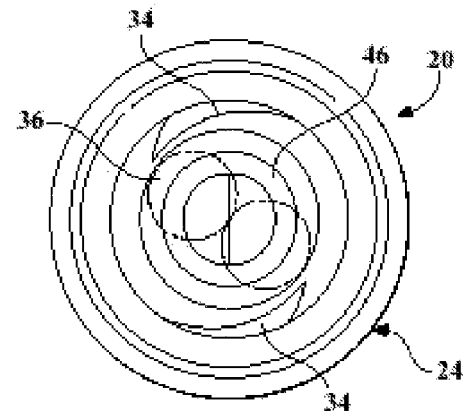
FIG. 7　　　　　FIG. 8A
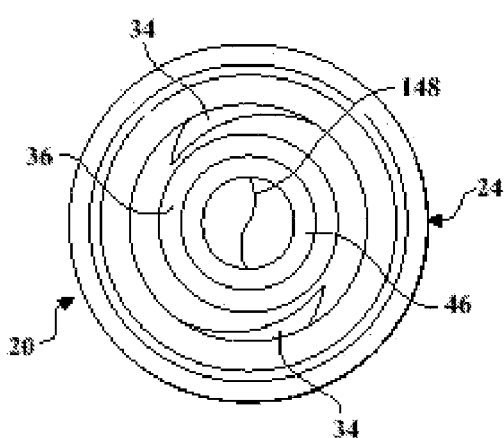
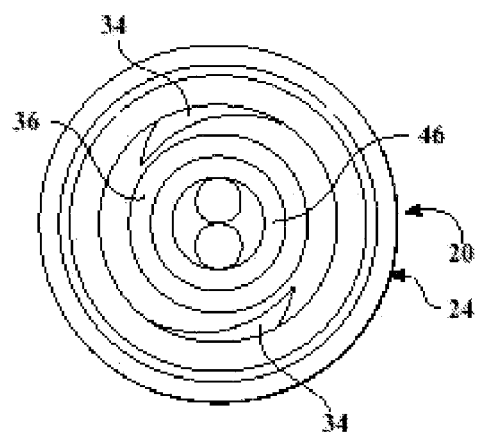
FIG. 8B　　　　　FIG. 9A
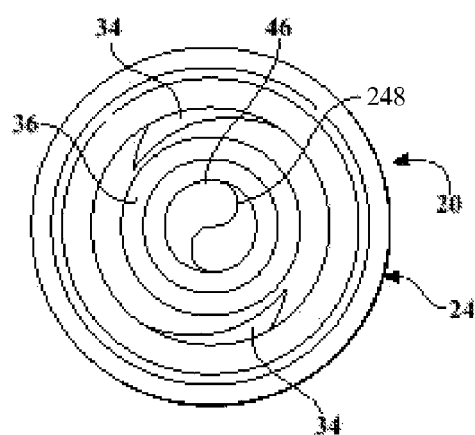
FIG. 9B

MEDICAL VALVE ASSEMBLY

CROSS REFERENCE TO RELATED APPLICATION

This application claims the benefit of provisional application Ser. No. 61/392,063 filed Oct. 12, 2010 and of provisional Ser. No. 61/474,925, filed Apr. 13, 2011.

BACKGROUND OF THE INVENTION

1. Field of the Invention

The invention relates to a medical valve assembly for receiving a fluid from a needleless syringe.

2. Description of the Prior Art

Needleless syringes are used in the medical field to deliver fluids to a patient without the risk of an accidental needle poke on either the patient or the person treating the patient. Needleless syringes generally include a luer for delivering the fluid to a medical valve and threads for threadedly engaging the medical valve. Various medical valves have been developed to engage the needleless syringes and deliver the fluid to an IV line of a patient. One such medical valve is shown in U.S. Pat. No. 6,651,956, issued to Pavel T. Miller on Nov. 25, 2003 (hereinafter referred to as "Miller '956"). The Miller '956 valve includes a housing; a receiver; and a valve stem presenting passageway and a stem slit for opening to receive the luer of the needleless syringe. The valve stem has an outer wall including a notch, which creates a gap between the internal wall of the housing and the outer wall of the valve stem. In operation, the luer of the needleless syringe is inserted into the stem slit of the valve stem and the valve stem buckles outwardly into the gap at the notch to provide room for the luer to penetrate into the passageway of the valve stem. This buckling movement of the valve stem changes the volume of the passageway and requires wasted space to allow for the valve stem to buckle outwardly.

When connected to an indwelling catheter, such medical valves provide a direct pathway for the infusion of fluids and medications into the vascular system of the patient. However this open pathway can also lead to the serious patient complications, if left unattended. It is a common practice to infuse fluids and medications by hanging a saline bag on an IV pole and permitting the gravity flow of fluid into the patient through an IV tube connected to the medical valve. If the attending staff are not vigilant, air can also enter the patient after all fluid has been infused. The resulting air embolism can cause significant patient morbidity or death. This can be prevented by placing a one way valve, or a check valve, between the needle free adapter and the IV tubing; however, this solution may be costly, a suitable check valve may not be available, and the additional connections and disconnections can be a source of contamination. Furthermore, check valves generally prevent the aspiration of blood for sampling to assess the patient's condition, thus requiring a separate valve for this process.

There remains a continuing need for improved medical valves for receiving needleless syringes.

SUMMARY OF THE INVENTION

According to one aspect of the invention, the medical valve assembly includes a housing, a receiver, and a valve stem. The valve stem presents a passageway for the flow of fluid and is of a resilient material, such as silicone, for resiliently deforming when the luer of a needleless syringe is inserted into the valve stem through the stem slit. The passageway of the valve stem has an hourglass shape for bulging inwardly in response to compression of the valve stem. Because of the hourglass shape, the volume of the passageway is decreased as compared to a valve stem having straight inner walls which could lead to a reduced risk of infection from fluids remaining in the passageway when the medical valve assembly is not in use. This reduction of the inner diameter of the fluid pathway creates a venturi effect when fluid is infused rapidly, such as during flushing of the valve. This venturi effect results in a more effective and efficient cleaning of the interior surfaces of the fluid pathway, thereby ensuring that blood is completely removed. This efficient design permits a minimal amount of saline flush to achieve the desired result without the use of heparin, which is contraindicated in neonates and immune surpressed patients. In other words, the medical valve assembly is more safe and sanitary than the medical valve assemblies of the prior art.

According to another aspect of the invention, the valve stem defines a point of reduced wall thickness, or a point of weakness, for deforming and collapsing a portion of the valve stem inwardly and downwardly into the housing at the point of weakness. The volume of the passageway of the valve stem remains relatively constant when this portion of the valve stem buckles and subsequently returns to its resting space after the luer of the needleless syringe is removed. This has the effect of reducing aspiration of the fluid when the luer of the needleless syringe is removed from the valve stem.

The medical valve assembly permits infusion of fluids as well as aspiration of blood samples. In addition, the medical valve is designed to prevent the inadvertent aspiration of air into the patient by stopping the fluid meniscus before it reaches the needleless syringe. Thus, the mechanism improves patient safety and reduces staff stress, thus permitting the staff to attend to more urgent matters.

According to yet another aspect of the invention, the medical valve assembly includes a bi-directional disc valve, which provides a safety mechanism to prevent exsanguination in the event of failure of the valve stem. The disc valve is never exposed to the perforation in the valve stem and responds only to differential pressure. The disc valve may additionally be calibrated to permit flow of fluid from the patient only in response to a higher pressure than those generated in the vascular system.

According to a further aspect of the invention, the medical valve assembly is smaller and more comfortable for the patient than the prior art medical valve assemblies because the valve stem collapses inwardly and downwardly at the point of weakness rather than buckling outwardly. This eliminates the need for a gap between the inner wall of the housing and the outer wall of the valve stem.

According to an additional aspect of the invention, all of the internal surfaces of the inner stem wall of the valve stem are smooth and rounded, i.e. there are no internal ribs or sharp corners. This reduces the chance that blood coagulates or other particulates will get trapped inside of the valve stem upon disconnection of the needleless syringe, thereby contaminating the valve stem.

According to yet another aspect of the invention, the valve stem presents a first stem end flush with a first housing end to seal the valve stem to the housing. The first stem end can be quickly and easily wiped clean between uses of the medical valve assembly.

According to another aspect of the invention, the housing of the medical valve has a housing exterior wall presenting threads for engaging the needleless syringe. The housing exterior wall defines a shoulder to present a stopping point for the needleless syringe. In other words, the needleless syringe can only be threaded onto the housing up to the shoulder. The shoulder prevents the luer from being inserted too far into the housing and also prevents the needleless syringe from being overtightened onto the housing, which can crack the rigid housing. This feature is also designed to limit the penetration of the luer into the passageway (lumen) of the valve stem, thereby displacing less volume than other designs. The reduced displaced volume reduces both negative pressure and negative displacement of fluid when the needleless syringe is disconnected.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 7 is a top view of the first exemplary embodiment wherein the valve stem includes a linear stem slit;

FIG. 8a is a top view of the first exemplary embodiment and showing exemplary circles in dashed lines for shaping an alternate stem slit;

FIG. 8b is a top view of the first exemplary embodiment and wherein the valve stem has a reverse-S shape;

FIG. 9a is a top view of the first exemplary embodiment and showing exemplary circles different than the circles of FIG. 8a for shaping a different alternate stem slit;

FIG. 9b is a top view of the first exemplary embodiment and wherein the valve stem has a reverse-S shape different than the stem slit of FIG. 8b;

FIG. 11b is a cross-sectional view of the exemplary disc valve taken along line B-B of FIG. 11a.

DETAILED DESCRIPTION OF THE ENABLING EMBODIMENTS

Figure 1:
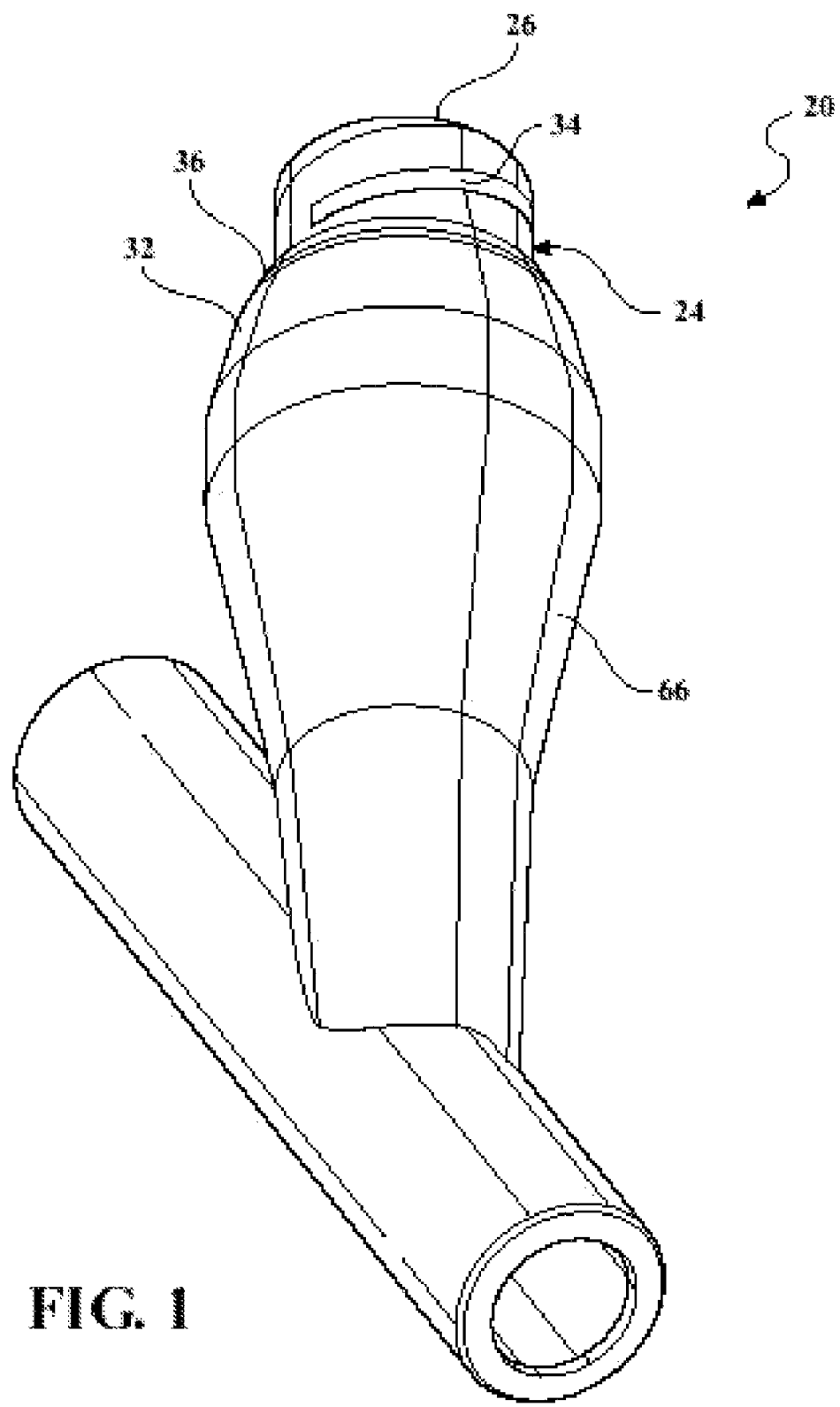
FIG. 1 is a perspective view of a first exemplary embodiment of the medical valve assembly.

Referring to the Figures, wherein like numerals indicate corresponding parts throughout the several views, a first exemplary embodiment of a medical valve assembly 20 for receiving a fluid from a needleless device is generally shown in FIG. 1. The needleless device is hereinafter referred to as a needleless syringe 22, though it should be appreciated that the needleless device could be any desirable device for injecting and/or ejecting a fluid.

The first exemplary medical valve assembly 20 includes a rigid external housing 24, generally indicated, extending along an axis A from an open first housing end 26 to an open second housing end 28. Preferably, the housing 24 is made of a polymeric material, but it should be appreciated that the housing 24 can be made of any rigid material. The housing 24 defines a housing inner wall 30 and a housing exterior wall 32, which defines threads 34 adjacent to the first housing end 26 for threadedly engaging the needleless syringe 22. The housing exterior wall 32 further defines a shoulder 36, which defines a stopping point for the needleless syringe 22 or other similar device used in IV infusion. As will be discussed in greater detail below, when the needleless syringe 22 is threaded by a predetermined distance onto the threads 34 of the housing 24, the needleless syringe 22 will abut the shoulder 36 to prevent further threading. This protects the medical valve assembly 20 by preventing the luer 38 of the needleless syringe 22 from being inserted too far into the medical valve assembly 20 and by preventing the needleless syringe 22 from being over tightened onto the housing 24, which could crack the rigid housing 24.

Figure 3:
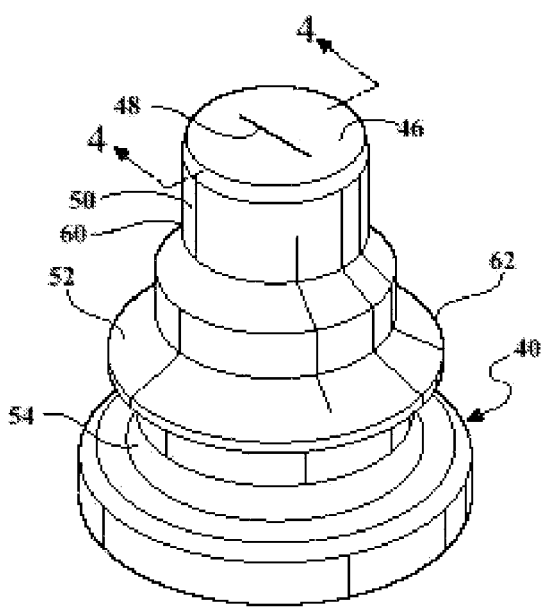
FIG. 3 is a perspective view of the valve stem.

The first exemplary medical valve assembly 20 also includes a valve stem 40, which is generally indicated in FIG. 1 and generally shown in FIG. 3. As shown in FIGS. 6a-e, the valve stem 40 is disposed in the housing 24 and extends along the axis A between the first and second housing ends 26, 28. The valve stem 40 receives the luer 38 of the needleless syringe 22 and prevents the fluid from flowing out of the housing 24 upon removal of the male luer 38. To accomplish this, the valve stem 40 has an outer stem wall that engages and is sealed to the housing inner wall 30 and an inner stem wall 42 presenting a passageway 44 for conveying the fluid through the valve stem 40. The valve stem 40 is preferably made of a resilient material for resiliently deforming when the male luer 38 of the needleless syringe 22 is inserted into the valve stem 40 and for returning to a relaxed, or uncompressed, position when the male luer 38 has been removed from the valve stem 40. The valve stem 40 is preferably made of a silicone material having a durometer in the range of 25 to 65. The silicone material is also preferably lubricated to reduce friction forces between the valve stem 40 and the housing 24. Among other options, the silicone can be prelubricated, the lubrication could be added during the injection molding process of forming the valve stem 40, or the silicone could be sprayed on the outside of the valve stem 40 after the valve stem 40 has been formed.

The valve stem 40 has a first stem end 46 extending radially inwardly form the housing inner wall 30 to close the first housing end 26. When the valve stem 40 is in an uncompressed state, the first stem end 46 is flush with the first housing end 26 to provide a swabable surface for cleaning the valve stem 40 between uses. The first stem end 46 further presents a stem slit 48 which is normally closed and opens to receive the male luer 38 of the needleless syringe 22, as will be discussed in further detail below. The stem slit 48 subsequently recloses when the luer 38 is withdrawn from the passageway 44 to prevent the entry of contaminates or the exit of the fluid from the valve stem 40. The stem slit 48 can be either cut straight across and through the first stem end 46, as shown in FIG. 7, or it could alternatively may have a reverse S-shape, the later of which is shown in FIGS. 8b and 9b. The purpose of the reverse-S shaped stem slit 148, 248 is to relieve stresses created at either end of the slit created by the clockwise rotation of the needleless syringe 22 from threading it onto the external housing 24 A reduction of mechanical stress at the endpoints of the stem slit 48, 148, 248 reduces the potential of tearing of the silicone, thereby prolonging the life of the valve stem 40 and increasing the number of times the medical valve assembly 20 may be used without compromising the integrity of the valve stem 40.

Figure 4:
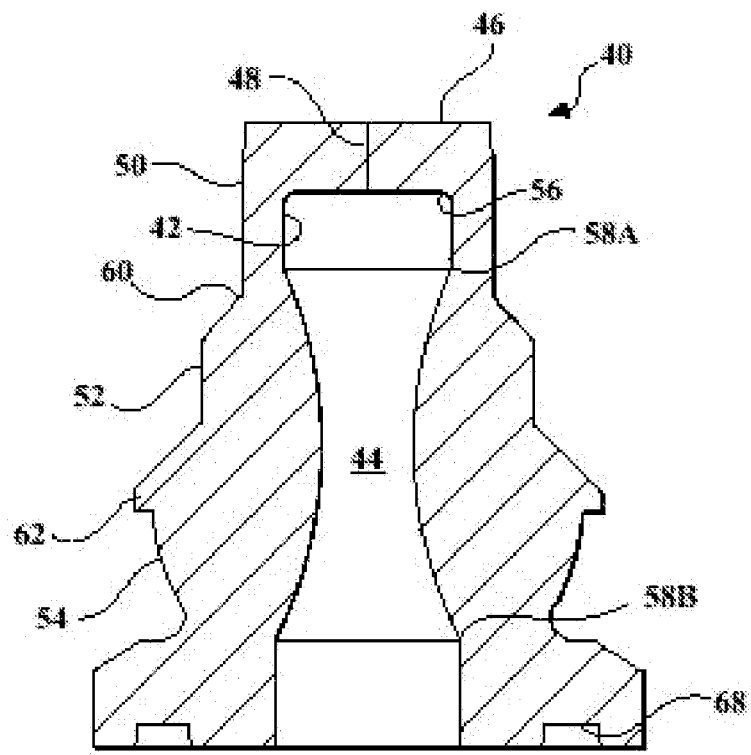
FIG. 4 is a cross-sectional view of the valve stem taken along line 4-4 of FIG. 3.
Figure 5:
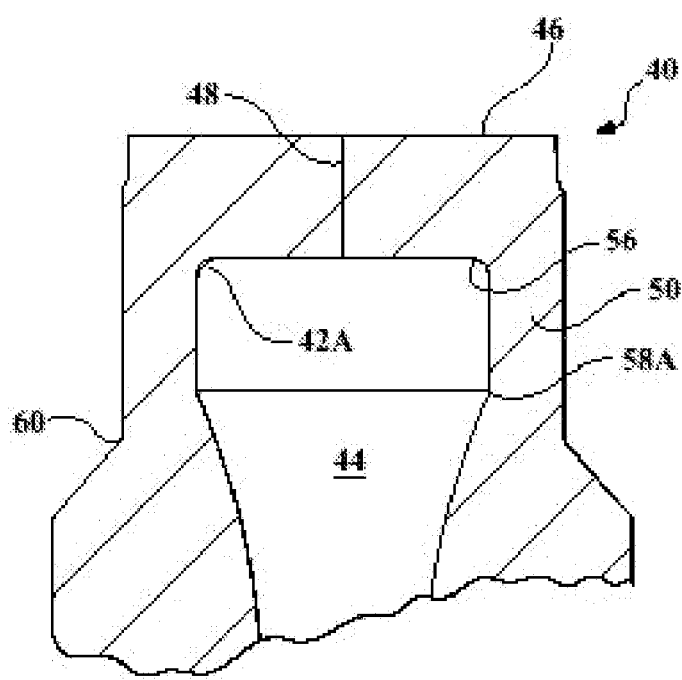
FIG. 5 is an enlarged view of the first stem end of FIG. 4.
Figure 6A:
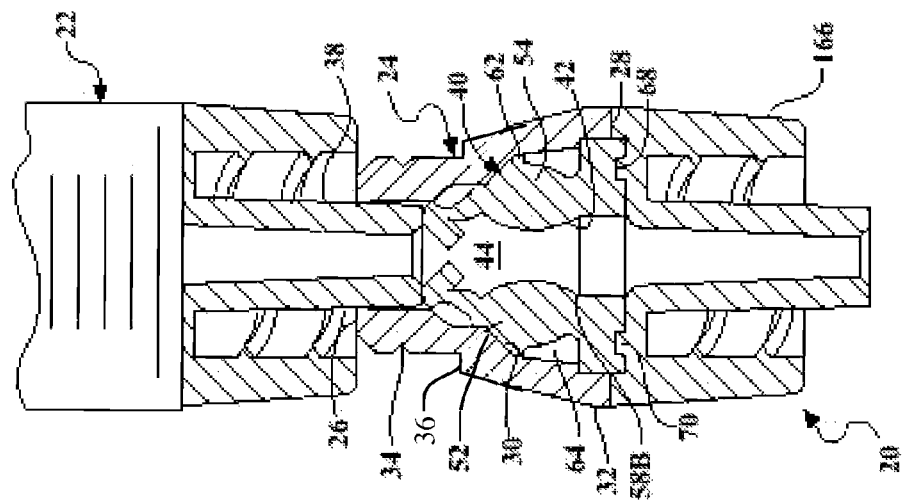
FIGS. 6a-6e are cross-sectional views of the valve first embodiment of the invention and showing the luer being inserted into the housing.
Figure 6B:
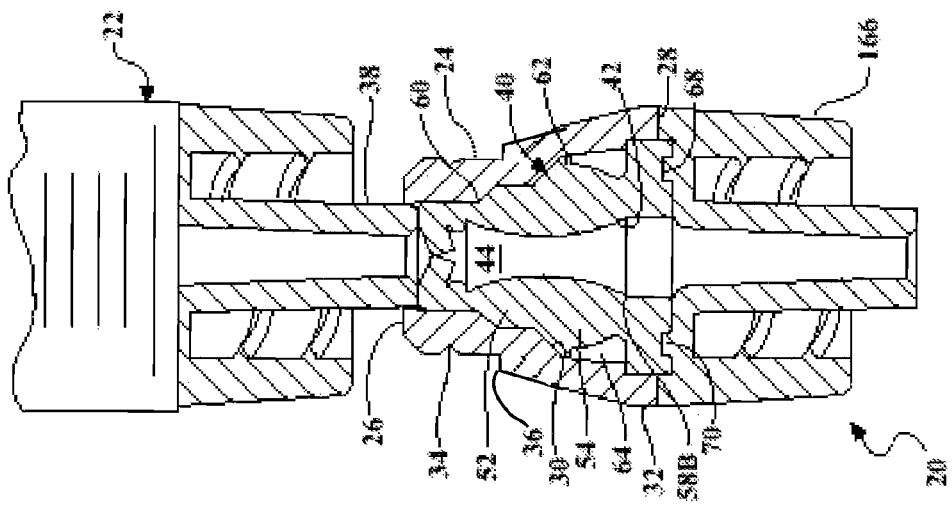
Figure 6C:
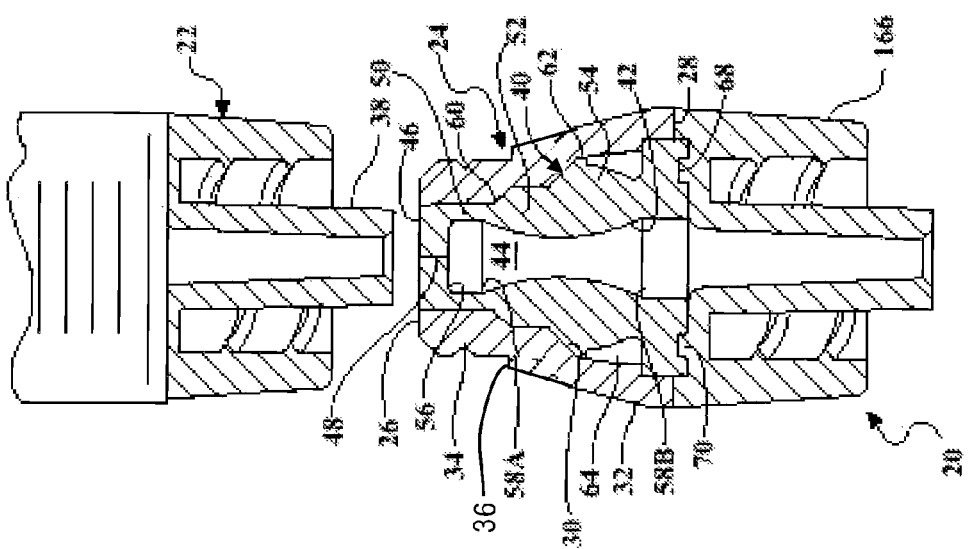
Figure 6D:
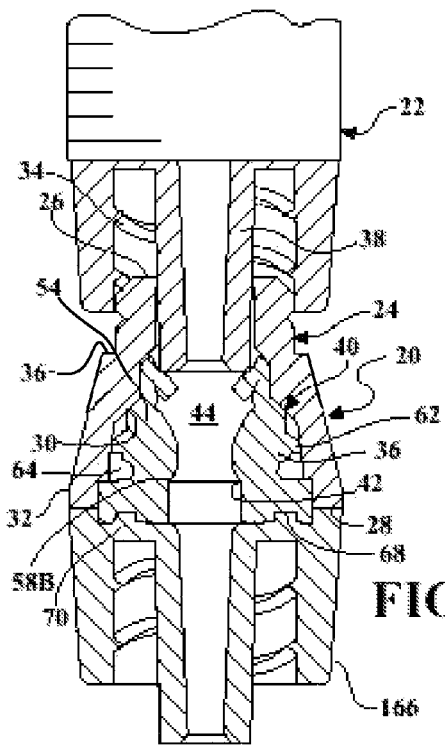
Figure 6E:
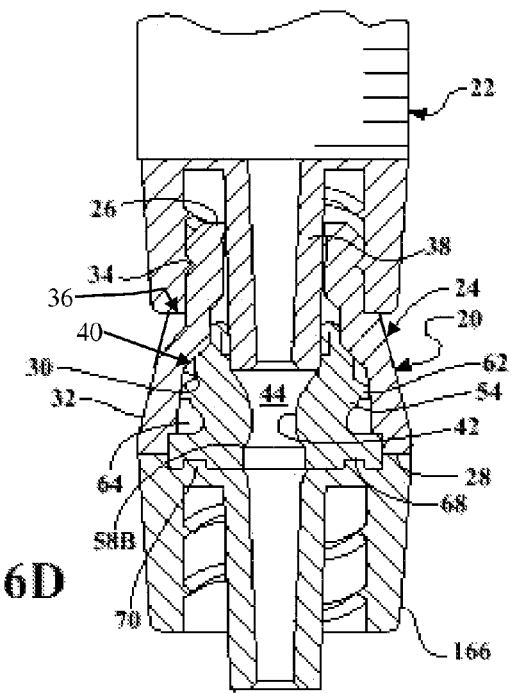

The valve stem 40 further defines a first stem portion 50 adjacent the first housing end 26, a second stem portion 52, and a third stem portion 54 adjacent the second housing end 28. As best shown in FIGS. 4 and 5, at the intersection of the first stem end 46 and the first stem portion 50, there is a fillet 56 which serves to strengthen the junction to resist torsional and axial stress. Additionally, all of the edges of the inner stem wall 42 of the valve stem 40 are rounded and smooth, i.e. there are no ribs or sharp corners. This reduces the chance that blood coagulates or other particulates, which could contaminate the valve stem 40, will get trapped inside of the passageway 44.

The first stem portion 50 has a generally cylindrical shape and extends axially along the housing inner wall 30 from the first stem end 46 to the second stem portion 52. As best shown in FIG. 4, the inner stem wall 42 is radiused inwardly from a point 58A on the inner stem wall 42 of the first stem portion 50 to a point 58B on the inner stem wall 42 of the third stem portion 54. The radius of the inner stem wall 42 of the second stem portion 52 bulges out into passageway 44 for conveying the fluid through the valve stem 40 to give the passageway 44 an hourglass shape. Because of the hourglass shape, the volume of the passageway 44 is decreased as compared to a valve stem 40 having straight inner walls, which could lead to a reduced risk of infection from fluids remaining in the passageway 44 when the medical valve assembly 20 is not in use.

The second stem portion 52 extends between the first and third stem portions 50, 54, and the outer stem wall of the second stem portion 52 slopes outwardly present a larger wall thickness in the second stem portion 52 relative to the first stem portion 50. The larger wall thickness of the second stem portion 52 urges the first stem portion 50 toward the first housing end 26 when the luer 38 is withdrawn from the valve stem 40. Likewise, the stem wall slopes outwardly in the third stem portion 54 to present a larger wall thickness for urging the second stem portion 52 to its uncompressed location when the luer 38 is withdrawn from the valve stem 40.

The valve stem 40 defines a point of reduced wall thickness in the valve stem 40, or a point of weakness 60, at the intersection of the interior wall of the first and second stem portions 50, 52. As discussed in further detail below, the first stem portion 50 deforms and buckles inwardly and downwardly at the point of weakness 60 in response to the luer 38 being inserted into the stem slit 48 of the first stem end 46.

In the exemplary valve stem 40, the outer stem wall in the third stem portion 54 defines a lip 62 and an open area 64. As shown in FIGS. 6a-e, when the needleless syringe 22 is threaded onto the threads 34 of the external housing 24 wall, the valve stem 40 deforms by a predetermined distance before the stem slit 48 opens to allow the insertion of the luer 38 into the passageway 44. The open area 64 functions to reduce the friction between the valve stem 40 and the inner housing 24 wall during the deformation of the valve stem 40. As the valve stem 40 compresses and deforms, the lip 62 is guided along the housing inner wall 30 of the housing 24.

The collapsing of the first stem portion 50 of valve stem 40 inwardly and downwardly at the point of weakness 60 and then the subsequent urging of the valve stem 40 back toward the first housing end 26 upon the removal of the needleless syringe 22 reduces the likelihood that any of the fluid will get trapped around the valve stem 40, thereby contaminating the valve stem 40. The opening of the stem slit 48 in the first stem end 46 provides a pathway for fluid exchange between the passageway 44 of the valve stem 40 and the needleless syringe 22. The outside edges of the first stem end 46 act as a seal about the luer 38 to prevent the escape of fluid about the valve stem 40. Additionally, the volume of the passageway 44 of the valve stem 40 changes very little when the valve stem 40 collapses downwardly at the point of weakness 60. There is a risk that the fluid will aspirate when the internal chamber expands in the prior art medical valve assemblies, but that risk is minimized with the exemplary medical valve assembly 20.

The shoulder 36 (discussed above) is specifically positioned for allowing the luer 38 of the needleless syringe 22 to penetrate the stem slit 48 while minimizing entry of the luer 38 into the passageway 44. In other words, the shoulder 36 is designed to limit the axial travel of the luer 38. As such, the negative displacement which occurs upon removal of the luer 38 during detachment is limited.

Figure 2:
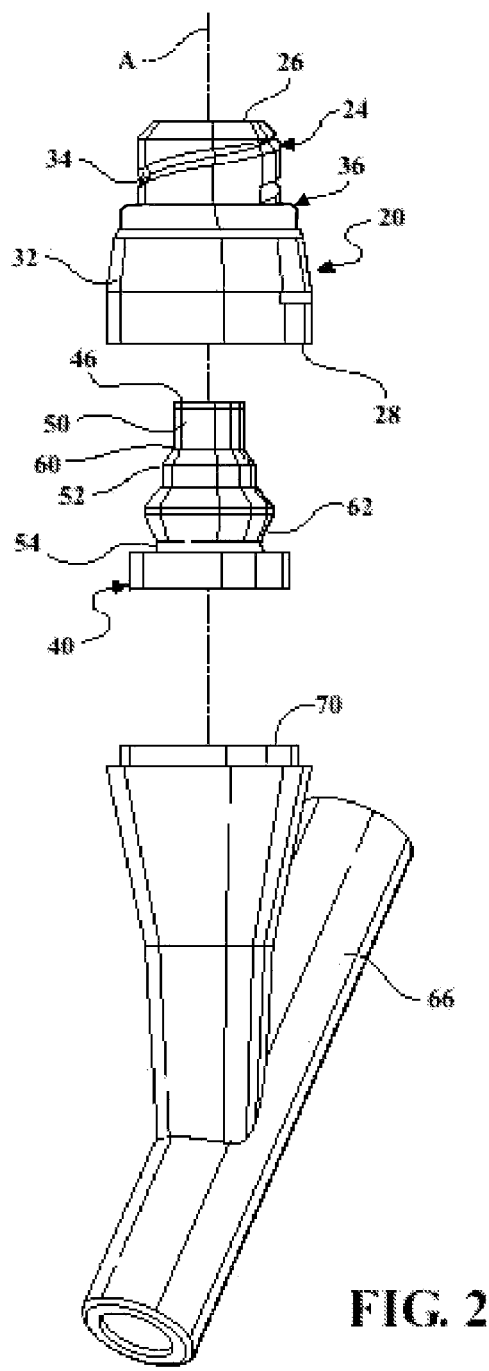
FIG. 2 is a perspective and exploded view of the first exemplary embodiment of the medical valve assembly.

The medical valve assembly 20 further includes a receiver 66, 166 mechanically engaging the second housing end 28 of the housing 24 for receiving the fluid delivered to the passageway 44 by the needleless syringe 22. The receiver 66 of the exemplary embodiment of FIGS. 1 and 2 is a Y-connector for conveying the fluid from the passageway 44 into a tube, whereas the receiver 166 of FIGS. 6a-e is a hose connector for mating with and delivering the fluid into an IV line or any other hose. The receiver 66, 166 is preferably ultrasonically welded to the housing 24, but any other method of connecting the receiver 66, 166 to the housing 24 may be used. As shown in FIG. 6, the valve stem 40 is compressed and captured between the housing 24 and the receiver 66, 166 to form a tight seal and prevent the fluid from leaking out of the medical valve assembly 20 where the housing 24 and receiver 66, 166 meet. As best shown in FIG. 4, the valve stem 40 contains a positioning recess 68 which mates with a positioning ridge 70 on the receiver 66, 166, thus capturing the valve stem 40 between the housing 24 and receiver 66, 166.

Figure 11A:
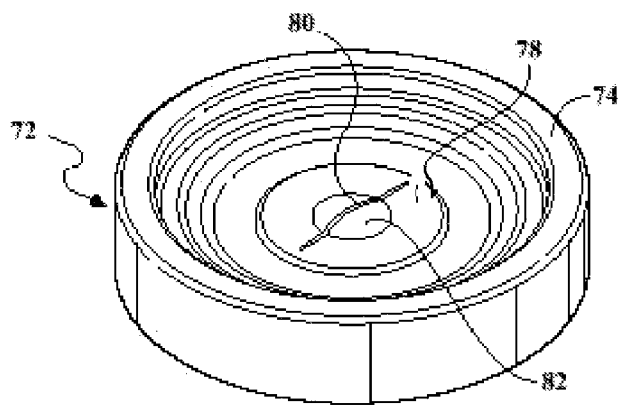
FIG. 11a is a perspective view of an exemplary disc valve.
Figure 11B:
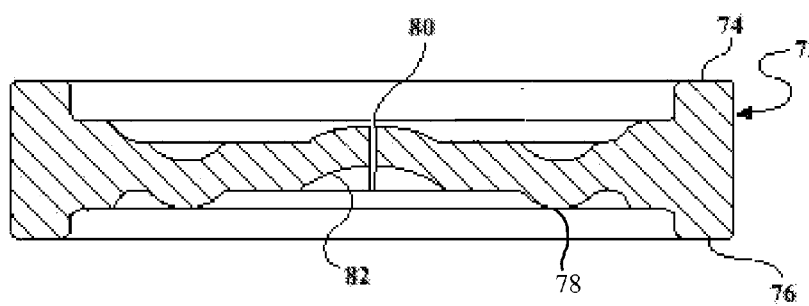
Figure 10:
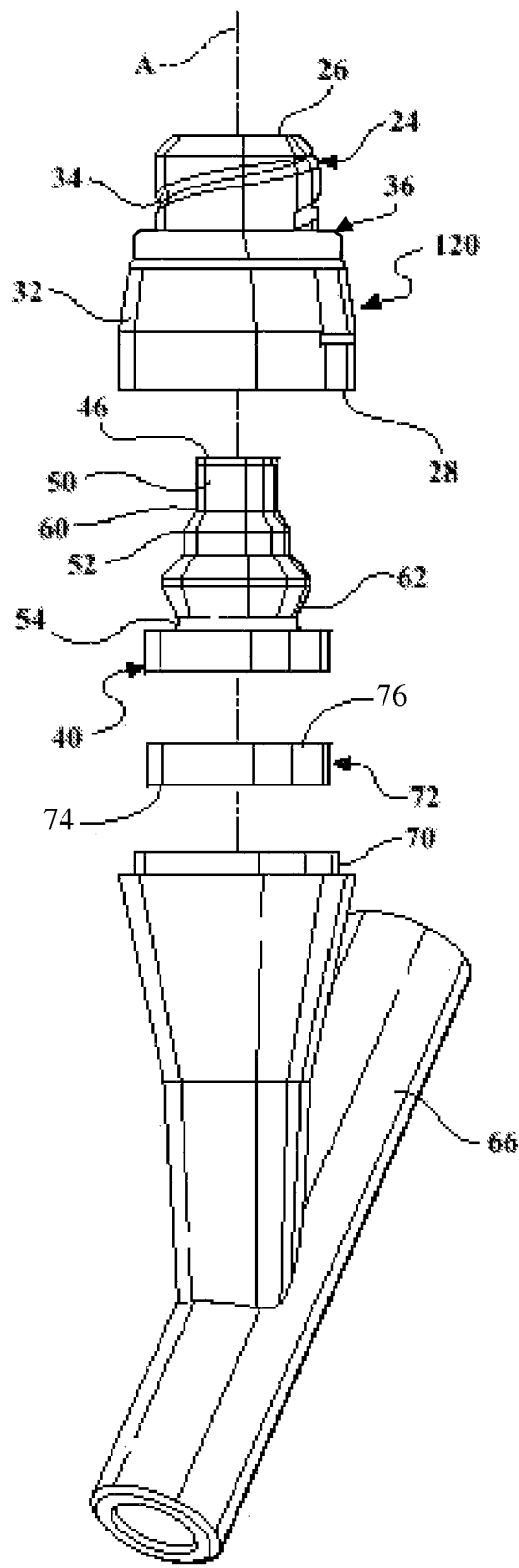
FIG. 10 is a perspective and exploded view of the second exemplary embodiment of the medical valve assembly.

As shown in FIG. 10, the second exemplary medical valve assembly 20 includes a valve disc 72, generally indicated, disposed at the second housing end 28 of the housing 24 for restricting the flow of the fluid therethrough and out of the housing 24. The valve disc 72 presents an upstream side 76 facing the first housing end 26 and a downstream side 74 facing the receiver 66, 166. The valve disc 72 further defines a circumferential raised rib 78 extending from the upstream side 76 of the valve disc 72, and a disc slit 80 for allowing the fluid to flow through the valve disc 72 in response to the pressure of the fluid being greater on one side of the valve disc 72 than on the other side of the valve disc 72. In other words, pressure in the fluid opens and closes the disc slit 80 to allow the fluid to flow therethrough. As shown in FIGS. 11a-b, the upstream side 76 of the valve disc 72 defines a dimple 82 at the disc slit 80 for reducing the pressure difference required to convey the fluid from the upstream side 76 of the valve disc 72 through the valve disc 72 relative to the pressure difference required to convey the fluid from the downstream side 74 of the disc through the disc. In other words, the dimple 82 allows fluid to flow more easily through the disc slit 80 in one direction relative to the other direction. When valve disc 72 is combined with valve stem 40, as illustrated in FIG. 10, the negative pressure created by the detachment of a luer 38 is insufficient to cause fluid flow to pass through disc slit 80 from the downstream side 74 to the upstream side 76, thereby eliminating displacement of fluid on the downstream side 74 of valve disc 72. In other words the combination of disc and valve stem 40 creates a near zero displacement valve. In a further embodiment, the elastic characteristics of valve disc 72 can be modified such that the valve disc 72 will be drawn toward external housing 24 upon withdrawal of the luer 38 without opening disc slit 80. Immediately upon withdrawal of the luer 38, the valve disc 72 will snap back to its resting position, forcing a positive displacement of fluid downstream from the downstream side 74 of disc valve and out the passageway 44 of the luer 38.

The valve disc 72 could also include a positioning ridge for mating with the positioning recess 68 of the valve stem 40 to seal the valve stem 40 and the valve disc 72 together. Even further, the valve disc 72 can be easily inserted into an existing valve assembly for controlling the flow of the fluid through the valve assembly.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A medical valve assembly for receiving a luer of a needleless syringe comprising:
    a rigid external housing extending along an axis from an open first housing end to an open second housing end;
    a valve stem disposed in said housing and extending from a first stem end defining a slit to a second stem end;
    said valve stem presenting a passageway extending from said slit to said second stem end for conveying a fluid therebetween;
    said valve stem being of a resilient material for compressing in response to pressure from the luer and wherein said slit on said first stem end opens to receive said luer within said slit in response to said valve stem being compressed by a predetermined distance; and
    wherein said passageway of said valve stem has a single hourglass shape for bulging inwardly in response to compression of said valve stem, wherein said hourglass shape includes a single inward bulge.

2. The medical valve assembly as set forth in claim 1 wherein said first stem end of said valve stem is generally flush with said open first housing end when said valve stem is uncompressed.

3. The medical valve assembly as set forth in claim 1 wherein said external housing presents an exterior wall presenting threads for threadedly engaging the needleless syringe.

4. The medical valve assembly as set forth in claim 3 wherein said exterior wall further presents a shoulder for limiting the axial travel of the luer into said passageway of said valve stem.

5. The medical valve assembly as set forth in claim 1 wherein said slit has a reverse-S shape.

6. The medical valve assembly as set forth in claim 5 wherein said slit bisects the center of said first stem end.

7. The medical valve assembly as set forth in claim 1 wherein said valve stem is of a material having a durometer in the range of 25 to 65.

8. The medical valve assembly as set forth in claim 7 wherein said valve stem is of silicone.

9. The medical valve assembly as set forth in claim 8 wherein said silicone of said valve stem is pre-lubricated for reducing friction between said valve stem and said external housing.

10. The medical valve assembly as set forth in claim 1 further including a receiver engaging said second housing end of said external housing for receiving the fluid from said passageway.

11. The medical valve assembly as set forth in claim 10 wherein said receiver is ultrasonically welded to said external housing.

12. The medical valve assembly as set forth in claim 10 wherein said second stem end of said valve stem presents a positioning recess and wherein said receiver presents a positioning ridge for mating with said positioning recess to capture said valve stem between said external housing and said receiver.

13. The medical valve assembly as set forth in claim 1 further including a disc valve disposed at said second housing end for restricting the flow of fluid therethrough and out of said passageway.

14. The medical valve assembly as set forth in claim 13 wherein said disc valve includes a raised rib presenting a disc slit for allowing the fluid to flow through said disc valve in response to the pressure of the fluid being greater on one side of said disc valve than on the other side of said disc valve.

15. The medical valve assembly as set forth in claim 13 further including a receiver engaging said second housing end of said external housing for receiving the fluid from said passageway and wherein said disc valve is disposed between said valve stem and said receiver.

16. The medical valve assembly as set forth in claim 1 wherein said valve stem further includes a first stem portion having a generally cylindrical shape and wherein said first stem portion deforms inwardly and downwardly in response to pressure from the luer to open said slit.

17. The medical valve assembly as set forth in claim 16 wherein said valve stem further includes second stem portion and a third stem portion presenting an open area for reducing friction between said third stem portion and said valve stem during compression of said valve stem.

18. The medical valve assembly as set forth in claim 17 wherein said second stem portion has a larger wall thickness than said first and third stem portions for expanding said valve in response to said luer being withdrawn.

19. The medical valve assembly as set forth in claim 17 wherein said valve stem includes an inner stem wall which defines said passageway and wherein said inner stem wall is radiused inwardly from a point in the first stem portion to a point in said third stem portion to define said hourglass shape.

20. The medical valve assembly as set forth in claim 19 wherein all of the edges of said inner stem wall are rounded.

21. A medical valve assembly for receiving a luer of a needleless syringe comprising:
    a rigid external housing extending along an axis from an open first housing end to an open second housing end;
    a valve stem disposed in said housing and extending from a first stem end defining a slit to a second stem end;
    said valve stem presenting a passageway extending from said slit to said second stem end for conveying a fluid therebetween;
    said valve stem being of a resilient material for compressing in response to pressure from the luer and wherein said slit on said first stem end opens to receive said luer within said slit in response to said valve stem being compressed by a predetermined distance; and
    wherein said passageway of said valve stem has an hourglass shape for bulging inwardly in response to compression of said valve stem, said hourglass shape having a single bulge and extending from a point adjacent to said slit to a point adjacent to said second stem end.

* * * * *